United States Patent
Thomas et al.

(10) Patent No.: US 10,822,320 B2
(45) Date of Patent: Nov. 3, 2020

(54) METHODS TO PURIFY CANNABINOIDS

(71) Applicant: Natural Extraction Systems, LLC, Boulder, CO (US)

(72) Inventors: C. Russell Thomas, Boulder, CO (US); Matthew M. DePalo, Broomfield, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 0 days.

(21) Appl. No.: 16/271,783

(22) Filed: Feb. 9, 2019

(65) Prior Publication Data

US 2020/0048215 A1  Feb. 13, 2020

Related U.S. Application Data

(60) Provisional application No. 62/803,409, filed on Feb. 8, 2019, provisional application No. 62/717,235, filed on Aug. 10, 2018.

(51) Int. Cl.
*C07D 311/78* (2006.01)
*B01D 5/00* (2006.01)

(52) U.S. Cl.
CPC ............ *C07D 311/78* (2013.01); *B01D 5/006* (2013.01)

(58) Field of Classification Search
CPC ............................. C07D 311/78; B01D 5/006
See application file for complete search history.

(56) References Cited

U.S. PATENT DOCUMENTS

| | | | |
|---|---|---|---|
| 4,396,487 A | 8/1983 | Strumskis | |
| 9,987,567 B1 | 6/2018 | Ko | |
| 10,159,908 B2 | 12/2018 | Thomas | |
| 10,195,159 B2 | 2/2019 | Whittle et al. | |
| 10,238,705 B2 | 3/2019 | Speier | |
| 2004/0147767 A1 | 7/2004 | Whittle et al. | |
| 2005/0042172 A1 | 2/2005 | Whittle | |
| 2009/0054711 A1 | 2/2009 | Lawrence et al. | |
| 2012/0157719 A1 | 6/2012 | Teles et al. | |
| 2018/0078874 A1 | 3/2018 | Thomas | |
| 2018/0296617 A1 | 10/2018 | Rivas | |
| 2019/0151171 A1 | 5/2019 | Johnson et al. | |
| 2020/0048214 A1 | 2/2020 | Thomas et al. | |
| 2020/0048215 A1 | 2/2020 | Thomas et al. | |

FOREIGN PATENT DOCUMENTS

| | | |
|---|---|---|
| CA | 2472561 A1 | 8/2002 |
| EP | 3453397 A1 | 3/2019 |
| JP | 4849578 B1 | 1/2012 |
| WO | WO-2002/089945 A2 | 11/2002 |
| WO | WO-2015/049585 A2 | 4/2015 |
| WO | WO-2016153347 A1 | 9/2016 |
| WO | WO-2016/161420 A1 | 10/2016 |
| WO | WO-2017/192527 A1 | 11/2017 |
| WO | WO-2018009514 A1 | 1/2018 |
| WO | WO-2018/102711 A1 | 6/2018 |
| WO | WO-2020/033859 | 2/2020 |
| WO | WO-2020/033864 | 2/2020 |

OTHER PUBLICATIONS

U.S. Appl. No. 16/271,782, Thomas et al.
U.S. Appl. No. 16/271,783, Metcalf et al.
U.S. Appl. No. 16/271,820, Metcalf et al.
International Search Report and Written Opinion for International Application No. PCT/US2019/045950 dated Nov. 15, 2019.
International Search Report and Written Opinion for International Application No. PCT/US2019/045960 dated Nov. 26, 2019.
Kanter et al., "Quantitative determination of detla9-tetrahydrocannabinol and delta9-tretrahydro-cannabinolic acid in marihuana by high-pressure liquid chromatography," J Chromatogr 171:504-508 (1979).
Veress et al., "Determination of cannabinoid acids by high-performance liquid chromatography of their neutral derivatives formed by thermal decarboxylation: I. Study of the decarboxylation process in open reactors," J Chromatogr, 520:339-347 (1990).
U.S. Appl. No. 16/271,782, Allowed.

*Primary Examiner* — Noble E Jarrell
(74) *Attorney, Agent, or Firm* — Foley Hoag LLP (57) ABSTRACT

Various aspects of this patent document relate to the rapid purification and decarboxylation of cannabinoids by vaporization and condensation.

26 Claims, 4 Drawing Sheets

METHODS TO PURIFY CANNABINOIDS

PRIORITY CLAIM

This patent application claims priority to U.S. Provisional Patent Application No. 62/717,235, filed Aug. 10, 2018, and U.S. Provisional Patent Application No. 62/803,409 filed Feb. 8, 2019, each of which is incorporated by reference in its entirety.

BACKGROUND

Industrial hemp and other forms of cannabis contain a variety of different cannabinoids, which predominantly each contain a carboxyl group. These cannabinoid carboxylic acids bind the human cannabinoid receptors with relatively low affinity. The production of therapeutic pharmaceuticals and psychoactive drugs from cannabis therefore generally utilizes a decarboxylation step, which typically involves prolonged heating. This heating also generally introduces other chemical modifications that are typically undesirable.

Marijuana produces tetrahydrocannabinolic acid ("THCA"), for example, which lacks robust pharmacological effects. THCA is converted into the psychoactive molecule tetrahydrocannabinol ("THC") by decarboxylation, which occurs when marijuana is smoked. THC is commercially produced from THCA by heating the THCA for several hours. Prolonged heating nevertheless results in undesirable side products. THCA can be oxidized, for example, into cannabinolic acid ("CBNA"), which decomposes into cannabinol ("CBN"). CBNA lacks well-known pharmacological properties, and CBN causes drowsiness.

Industrial hemp similarly produces cannabidiolic acid ("CBDA"), which lacks robust pharmacological effects. CBDA is converted into the pharmaceutical cannabidiol ("CBD") by decarboxylation. CBD is commercially produced from CBDA by heating the CBDA for several hours. Prolonged heating nevertheless results in undesirable side products including CBN.

The industrial production of decarboxylated cannabinoids also degrades and vaporizes other molecules found in cannabis including terpenes, terpene alcohols, terpenoids, and flavonoids, which often impart favorable characteristics to products containing cannabinoids including favorable flavor and aroma.

Improved methods to decarboxylate cannabinoids are desirable.

SUMMARY

Various aspects of this patent document relate to the rapid purification and decarboxylation of cannabinoids by vaporization and condensation.

DETAILED DESCRIPTION

The present disclosure describes methods to rapidly decarboxylate cannabinoids without generating appreciable quantities of undesirable side products. Various methods comprise (1) rapidly vaporizing and decarboxylating a cannabinoid, and then (2) contacting the vaporized, decarboxylated cannabinoid with a heat sink to condense the decarboxylated cannabinoid.

Cannabinoids are typically decarboxylated by heating. Traditional hydrocarbon-based extraction methods typically extract cannabinoid carboxylic acids from cannabis prior to decarboxylation. The extracted cannabinoid carboxylic acids are typically then converted into activated decarboxylated cannabinoids by heating in a vacuum oven for several hours. The inventors modelled possible reaction mechanisms for the decarboxylation and determined that cannabinoid carboxylic acids can self-catalyze the reaction.

Figure 1:
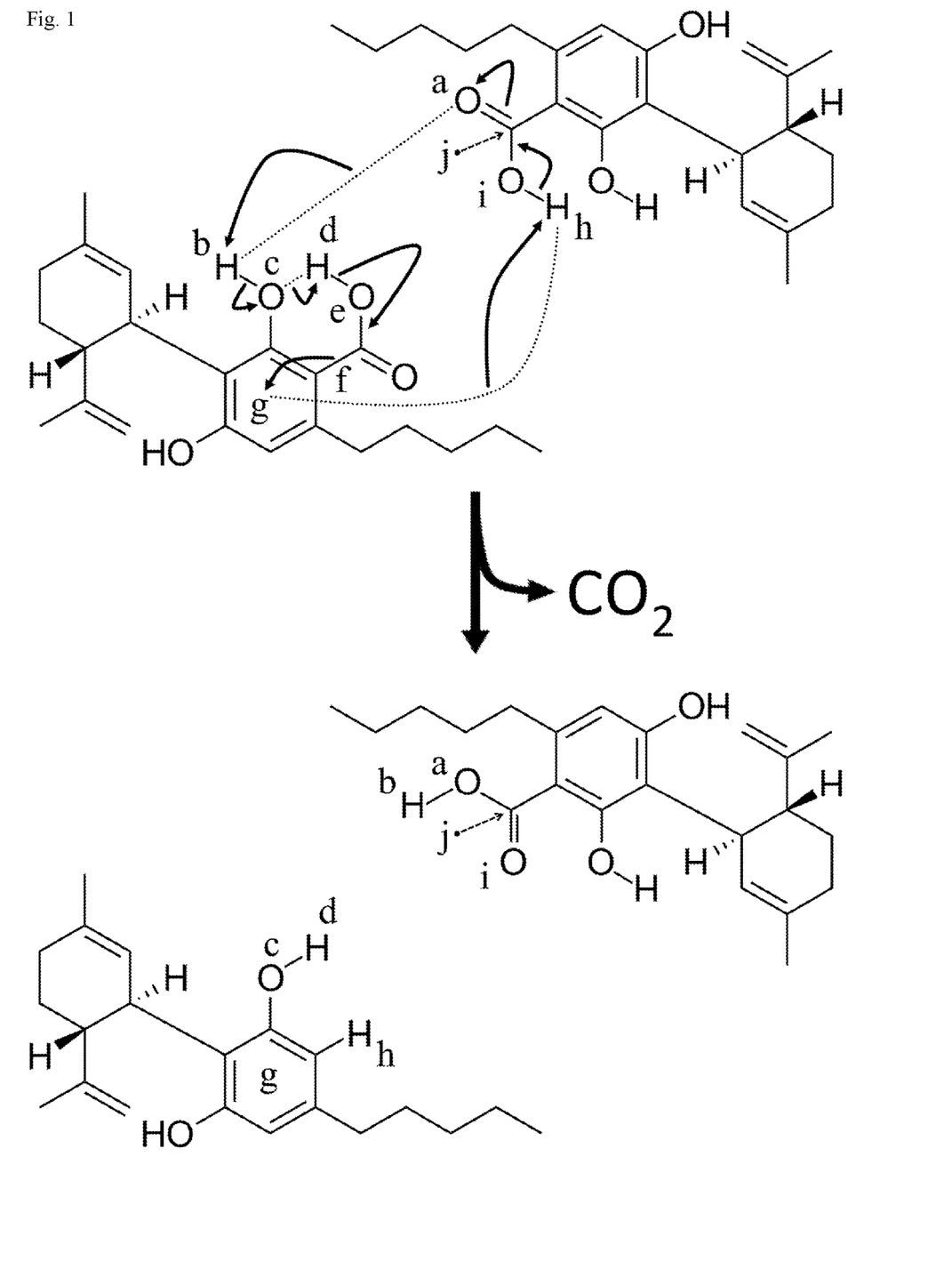
FIG. 1 depicts the skeletal formula of two CBDA molecules before a first CBDA molecule catalyzes the decarboxylation of a second CBDA molecule to regenerate the first CBDA molecule and to produce CBD and carbon dioxide from the second CBDA molecule.

According to the self-catalyzed reaction mechanism, decarboxylation can proceed in a single-step, cyclic reaction depicted in FIG. 1, which shows a first 2,4-dihydroxy-3-[(1R,6R)-6-isopropenyl-3-methylcyclohex-2-en-1-yl]-6-pentylbenzoic acid ("CBDA") molecule (FIG. 1, top) catalyzing the decarboxylation of a second CBDA molecule (FIG. 1, bottom). Immediately prior to the reaction, the first and second CBDA molecules form two intermolecular hydrogen bonds denoted by two long dotted lines in FIG. 1. The hydrogen bond depicted by the top-most dotted line is between an electron pair of the carbonyl oxygen of the first CBDA molecule (FIG. 1, "a") and the hydroxyl proton of the second CBDA molecule (FIG. 1, "b"). The hydrogen bond depicted by the bottom-most dotted is between the pi electron cloud of the second CBDA molecule (FIG. 1, "g") and the carboxylic acid proton of the first CBDA molecule (FIG. 1, "h"). An intramolecular hydrogen bond also forms between an electron pair of the hydroxyl oxygen of the second CBDA molecule (FIG. 1, "c") and the carboxylic acid proton of the second CBDA molecule (FIG. 1, "d").

The predicted, single-step, cyclic reaction shown in FIG. 1 proceeds by converting the three hydrogen bonds into covalent bonds, breaking four single bonds, converting two single bonds into double bonds, and converting a double bond into a single bond. The hydrogen bond between an electron pair of the carbonyl oxygen of the first CBDA molecule (FIG. 1, "a") and the hydroxyl proton of the second CBDA molecule (FIG. 1, "b") becomes a covalent bond, which converts the double bond between the carbonyl oxygen (FIG. 1, "a") and the carbonyl carbon (FIG. 1, "j") of the first CBDA molecule into a single bond. The hydroxyl of the second CBDA molecule reforms by converting the hydrogen bond between an electron pair of the hydroxyl oxygen of the second CBDA molecule (FIG. 1, "c") and the carboxylic acid proton of the second CBDA molecule (FIG. 1, "d") into a covalent bond. The extra electron pair of the deprotonated carboxylate oxygen of the second CBDA molecule (FIG. 1, "e") converts the single bond of the deprotonated carboxylate into a double bond, and the electron pair of the carbon-carbon single bond at the 1-position of the second CBDA molecule (FIG. 1, "f") enters the pi electron cloud of the aromatic ring of the second CBDA molecule (FIG. 1, "g") to release the deprotonated carboxylate from the second CBDA molecule as a carbon dioxide molecule. The hydrogen bond between the pi electron cloud of the second CBDA molecule (FIG. 1, "g") and the carboxylic acid proton of the first CBDA molecule (FIG. 1, "h") becomes a covalent bond to replace the deprotonated carboxylate at the 1-position of the second CBDA molecule (which left the second CBDA molecule as a carbon dioxide molecule) with the proton. The extra electron pair of the deprotonated oxygen of the first CBDA molecule (FIG. 1, "i") converts the single bond between the deprotonated oxygen (FIG. 1, "i") and the carbonyl carbon (FIG. 1, "j") into a double bond to reform the carboxylic acid of the first CBDA molecule.

The reaction mechanism described above is represented by arrows in FIG. 1, which depict electron pair pushing. Specific atoms are annotated by the lowercase letters "a"-"e" and "h"-"j" in FIG. 1 as described above. The bond that breaks to decarboxylate the second CBDA molecule and release a carbon dioxide molecule is annotated by the lowercase letter "f" in FIG. 1 as described above. The pi electron cloud of the aromatic ring of the second CBDA molecule is annotated by the lowercase letter "g" in FIG. 1 as described above.

The proposed reaction mechanism described above was modeled in three dimensions to determine whether the sterics of the actual CBDA and THCA molecules are compatible with the proposed reaction mechanism. The inventors determined that two CBDA or THCA molecules can form near-perfect hydrogen bond lengths and geometries without steric clashes or significant entropic penalty provided that a first CBDA or THCA molecule can interact with a second CBDA or THCA molecule at an approximate orthogonal orientation.

Figure 2:
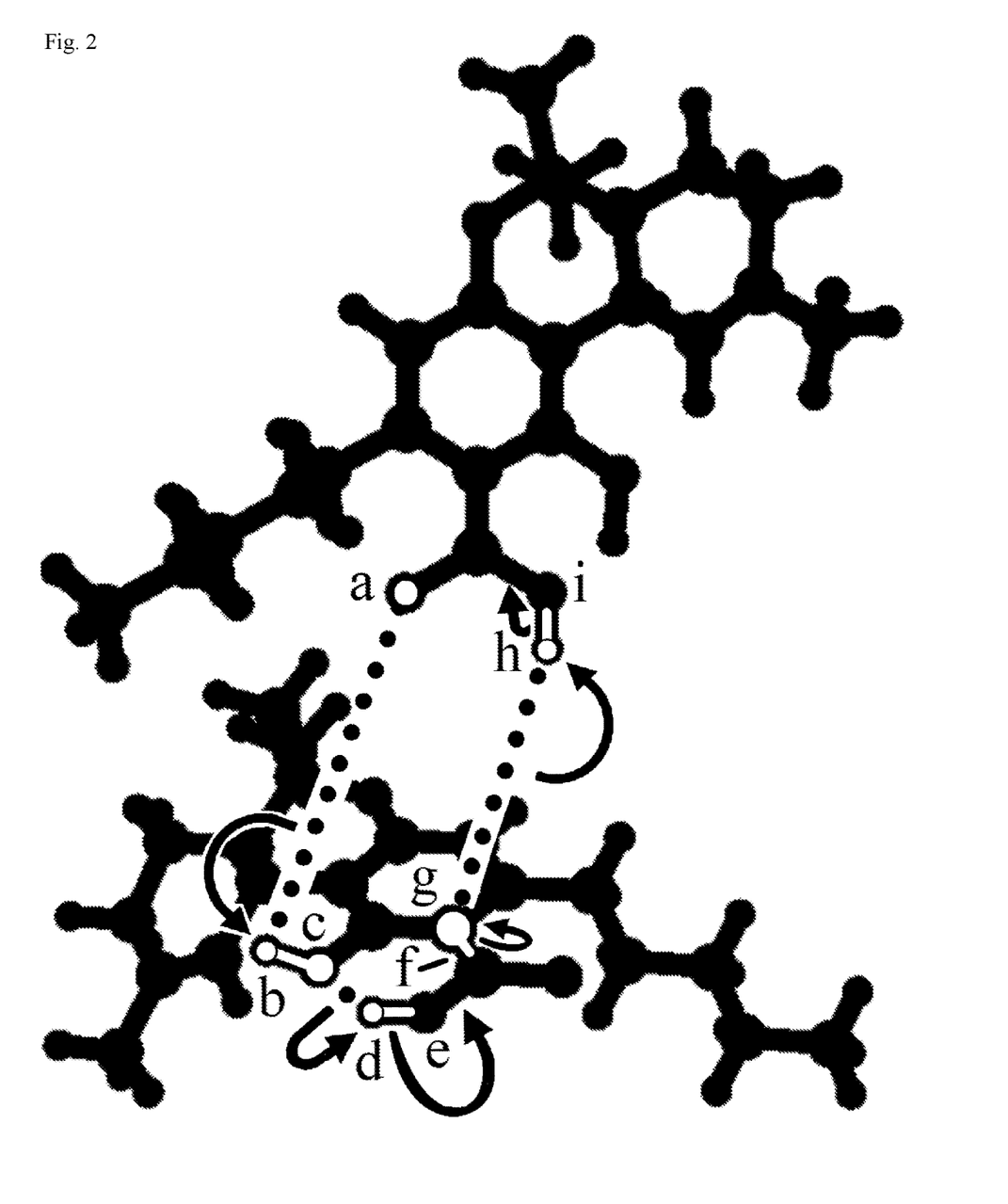
FIG. 2 is a ball and stick model of two THCA molecules, which depicts two intermolecular hydrogen bonds between the two THCA molecules and electron pair arrow pushing to show a predicted, single-step, cyclic chemical reaction catalyzed by a first THCA molecule that results in the decarboxylation of a second THCA molecule.

FIG. 2 shows a first (6aR,10aR)-1-hydroxy-6,6,9-trimethyl-3-pentyl-6a,7,8,10a-tetrahydro-6H-benzo[c]chromene-2-carboxylic acid ("THCA") molecule (FIG. 2, top) catalyzing the decarboxylation of a second THCA molecule (FIG. 2, bottom). Immediately prior to the reaction, the first and second THCA molecules form two intermolecular hydrogen bonds denoted by two long dotted lines in FIG. 2. The hydrogen bond depicted by the left-most dotted line is between an electron pair of the carbonyl oxygen of the first THCA molecule (FIG. 2, "a") and the hydroxyl proton of the second THCA molecule (FIG. 2, "b"). The hydrogen bond depicted by the right-most dotted is between the pi electron cloud of the second THCA molecule (FIG. 2, "g") and the carboxylic acid proton of the first THCA molecule (FIG. 2, "h"). An intramolecular hydrogen bond also forms between an electron pair of the hydroxyl oxygen of the second THCA molecule (FIG. 2, "c") and the carboxylic acid proton of the second THCA molecule (FIG. 2, "d").

The predicted, single-step, cyclic reaction shown in FIG. 2 proceeds by converting the three hydrogen bonds into covalent bonds, breaking four single bonds, converting two single bonds into double bonds, and converting a double bond into a single bond. The hydrogen bond between an electron pair of the carbonyl oxygen of the first THCA molecule (FIG. 2, "a") and the hydroxyl proton of the second THCA molecule (FIG. 2, "b") becomes a covalent bond, which converts the double bond between the carbonyl oxygen (FIG. 2, "a") and carbonyl carbon of the first THCA molecule into a single bond. The hydroxyl of the second THCA molecule reforms by converting the hydrogen bond between an electron pair of the hydroxyl oxygen of the second THCA molecule (FIG. 2, "c") and the carboxylic acid proton of the second THCA molecule (FIG. 2, "d") into a covalent bond. The extra electron pair of the deprotonated carboxylate oxygen of the second THCA molecule (FIG. 2, "e") converts the single bond of the deprotonated carboxylate into a double bond, and the electron pair of the carbon-carbon single bond at the 2-position of the 6H-benzo[c]chromene of the second THCA molecule (FIG. 2, "f") enters the pi electron cloud of the aromatic ring of the second THCA molecule (FIG. 2, "g") to release the deprotonated carboxylate from the second THCA molecule as a carbon dioxide molecule. The hydrogen bond between the pi electron cloud of the second THCA molecule (FIG. 2, "g") and the carboxylic acid proton of the first THCA molecule (FIG. 2, "h") becomes a covalent bond to replace the deprotonated carboxylate at the 2-position of the 6H-benzo[c]chromene of the second THCA molecule (which left the second THCA molecule as a carbon dioxide molecule) with the proton. The extra electron pair of the deprotonated oxygen of the first THCA molecule (FIG. 2, "i") converts the single bond between the deprotonated oxygen and carbonyl carbon into a double bond to reform the carboxylic acid of the first THCA molecule.

The reaction mechanism described above is represented by arrows in FIG. 2, which depict electron pair pushing. Atoms that form hydrogen bonds that become covalent bonds are shown with white fill in FIG. 2. Covalent bonds that break are shown with white fill in FIG. 2. Three hydrogen bonds that become covalent bonds are shown with dotted lines in FIG. 2. Specific atoms are annotated by the lowercase letters "a"-"e," "h", and "i" in FIG. 2 as described above. The bond that breaks to decarboxylate the second THCA molecule and release a carbon dioxide molecule is annotated by the lowercase letter "f" in FIG. 2 as described above. The pi electron cloud of the aromatic ring of the second THCA molecule is annotated by the lowercase letter "g" in FIG. 2 as described above.

The reaction mechanisms set forth above are descriptive approximations that conform with classical theories of organic chemistry. Other scientific theories such as quantum mechanical theory might describe the same chemical reaction differently and in a manner that contradicts the reaction mechanism set forth above. The precise description of the decarboxylation reaction mechanism is irrelevant to this patent document and any claim that matures from the disclosure of this patent document. Two insights obtained from this reaction mechanism are relevant: (1) a molecule having a functional group that is both a Brønsted acid and a Brønsted base (such as a carboxylic acid) can catalyze the decarboxylation of a cannabinoid, and (2) the accessible orientations between a cannabinoid and a catalyst affect the decarboxylation reaction rate.

An implication of the insights set forth above is that the activation energy of the cannabinoid decarboxylation reaction can be lowered by increasing the probability that a catalyst will contact a cannabinoid at an appropriate geometry to form two intermolecular hydrogen bonds between the catalyst and the cannabinoid. During self-catalysis in the liquid phase, cannabinoids preferably form roughly-parallel pi-stacking interactions that inhibit the formation of intermolecular hydrogen bonds having geometries capable of the cyclic decarboxylation reaction described above. Traditional decarboxylation by heating cannabinoids partially disrupts the pi-stacking interactions and introduces entropy, which each increase the probability that intermolecular hydrogen bonds will form that have an appropriate geometry and connectivity for the decarboxylation reaction. One inventive aspect of this patent document is the discovery that the activation energy can also be lowered by introducing entropy into the system through other means such as by vaporization.

Smoking and vaporizing marijuana are both known to decarboxylate cannabinoids, but smoking and vaporizing marijuana are not known to result in near-stoichiometric yields. Smoking degrades a substantial portion of cannabinoids by combustion, thermal oxidation, pyrolysis, and isomerization. Vaporization minimizes combustion, but vaporization nevertheless results in oxidation, pyrolysis, and isomerization.

Laboratory analyses suggest that commercially-available personal vaporizers are capable of variable decarboxylation efficiencies ranging from about 80% efficiency to near-complete decarboxylation when operated under laboratory conditions, but personal vaporizers generate substantial amounts of undesirable side products such as cannabinol. Consumers compensate for variable efficiency, oxidation, pyrolysis, and isomerization by simply titrating their dose. The laboratory analyses of consumer products that generate a vapor are informative, but these products are less relevant to commercial strategies to produce high-value liquid cannabinoids.

Attempts to decarboxylate cannabinoids by vaporization in industrial processes have met with limited success. The prior art discloses methods to decarboxylate cannabinoids from plant material by vaporization at a temperature of 145° C. (293° F.) for about 30 minutes, which resulted in a purported 95% decarboxylation efficiency (PCT Patent Application Publication No. WO 02/089945 A2). Actual yields relative to the amounts of cannabinoids in the starting materials were not reported. The prior art methods were also incapable of recovering high yields of decarboxylated cannabinoids without converting a substantial portion of the cannabinoids into undesirable degradation products such as cannabinol (PCT Patent Application Publication No. WO 02/089945 A2 at pages 41-43). The recovered cannabinoids included 6.2-14.1% cannabinol. Formulations comprising cannabinol at concentrations of 1% or greater as a percentage of total cannabinoids are typically useful only as sleep aids, and concentrations of 5% or greater cause extreme drowsiness. No known method allows for the purification of pharmacologically-relevant cannabinoids from cannabinol in a commercially-viable process, and thus, the prior art methods have limited commercial utility.

The inventors previously developed systems to extract cannabinoids by vaporization (for example, PCT Patent Application Publication No. WO 2015/049585 A2 and WO 2018/102711 A1). Vaporization generally requires high temperatures, which favor both undesirable pyrolysis and decarboxylation (i.e., desirable pyrolysis). The inventors previously disclosed methods that minimize or eliminate pyrolysis, which minimizes or eliminates decarboxylation by definition (for example, PCT Patent Application Publication No. WO 2015/049585 A2 and WO 2018/102711 A1). Cannabinoid carboxylic acids could be decarboxylated either before or after purification in a decarboxylation process that maximizes yield.

The inventors have now identified methods that decouple decarboxylation from other undesirable chemical reactions during vaporization, which are generally applicable to all known methods of vaporization. These methods are also surprisingly more efficient than prior art methods and allow simultaneous purification and decarboxylation.

The inventors identified parameters that result in marked improvements over prior art methods: (1) the cannabinoids should be present in a composition having a high surface-area-to-volume ratio, (2) the cannabinoids should be present in the composition at a relatively high concentration, and (3) cannabinoid vapor should be condensed immediately after vaporization. High surface area and high relative cannabinoid concentration ensures that the energy used to vaporize and decarboxylate a cannabinoid carboxylic acid favors vaporization and decarboxylation relative to the heating and vaporization of other molecules. Rapid condensation of cannabinoid vapor minimizes contact between cannabinoid vapor and other heated molecules.

Vaporizing a cannabinoid carboxylic acid does not necessarily result in decarboxylation, and vaporization often results in undesirable pyrolysis. When the above parameters are optimized, cannabinoid carboxylic acids can be both decarboxylated and vaporized at temperatures near or below their boiling points to allow simultaneous decarboxylation and purification and minimize undesirable pyrolysis.

The inventors contemplate that reducing the duration of time that heated cannabinoids spend in contact with other heated molecules reduces the rate of undesirable oxidation, pyrolysis, and isomerization of the cannabinoids. Surprisingly, reducing the duration of time that heated cannabinoids spend in contact with other heated molecules—and reducing the duration of time that cannabinoids are exposed to heat—nevertheless permits rapid and efficient decarboxylation and allows near-stoichiometric decarboxylation while minimizing oxidation, pyrolysis, and isomerization.

The conceptual framework described above allows for the minimization of the time and energy required to decarboxylate cannabinoids by minimizing the activation energy of the decarboxylation reaction. The conceptual framework similarly allows for the optimization of the power required to decarboxylate cannabinoids.

This patent document discloses for the first time that a cannabinoid can catalyze the decarboxylation of another cannabinoid.

This patent document discloses for the first time that the activation energy of the cannabinoid decarboxylation reaction can be minimized relative to prior art methods, and thus, the energy added during a decarboxylation reaction can be minimized relative to prior art methods.

This patent document discloses for the first time that the power driving the cannabinoid decarboxylation reaction can be optimized relative to prior art methods, and thus, the rate of a decarboxylation reaction can be maximized relative to prior art methods.

Various aspects of the disclosure relate to a method to purify a cannabinoid molecule from a non-volatile molecule.

In some embodiments, a method comprises providing a composition comprising a cannabinoid molecule and a non-volatile molecule. In some specific embodiments, a method comprises providing a composition comprising a cannabinoid molecule and a non-volatile molecule in which both the cannabinoid molecule and the non-volatile molecule are in a liquid phase or a solid phase. In some specific embodiments, the non-volatile molecule is cellulose.

In some embodiments, a method comprises contacting a composition with 50 joules to 100 kilojoules of energy per gram of the composition. In some specific embodiments, a method comprises contacting a composition with 50 joules to 100 kilojoules of energy per gram of the composition to convert a cannabinoid molecule of the composition into a vaporized cannabinoid molecule in a gas phase. In some very specific embodiments, a method comprises contacting a composition with 50 joules to 100 kilojoules of energy per gram of the composition to convert a cannabinoid molecule of the composition into a vaporized cannabinoid molecule in a gas phase without vaporizing a non-volatile molecule of the composition.

In some embodiments, a method comprises separating a vaporized cannabinoid molecule in a gas phase from a non-volatile molecule.

In some specific embodiments, a method comprises contacting a vaporized cannabinoid molecule with a heat sink to condense the vaporized cannabinoid molecule into a condensed cannabinoid molecule in a liquid distillate.

In some embodiments, a composition comprises a plant material. In some specific embodiments, a composition comprises a ground plant material. In some embodiments, a composition has a surface-area-to-volume ratio greater than 1000 per meter.

In some embodiments, a plant material is a species of the genus *Cannabis*. In some specific embodiments, a plant material is *Cannabis sativa*. In some specific embodiments, a plant material is *Cannabis indica*. In some specific embodiments, a plant material is *Cannabis ruderalis*. In some very specific embodiments, a plant material is *Cannabis sativa* forma *indica*. In some specific embodiments, a plant material lacks THC and potential THC at a combined concentration by weight exceeding 0.3%. The term "potential THC" refers to THCA multiplied by 314.47 (the molecular weight of THC) and divided by 358.48 (the molecular weight of THCA). A plant material that lacks THC and contains 0.33% THCA, for example, contains THC and potential THCA at a combined concentration by weight of 0.29%.

In some embodiments, a composition comprises an extracted oil from the genus *Cannabis*. In some specific embodiments, a composition comprises an extracted oil from industrial hemp. The term "industrial hemp" refers to *Cannabis sativa* forma *indica* that either is essentially free of THC and THCA or comprises THC and potential THC at a combined concentration by weight no greater than 0.3%.

In some embodiments, a composition comprises marijuana or a composition is derived from marijuana.

In some embodiments, a composition is a liquid such as an oil. In some embodiments, a composition is an aerosol. In some specific embodiments, a composition comprises a suspension of solid particles in a gas. In some specific embodiments, a composition comprises a suspension of liquid droplets in a gas.

In some specific embodiments, a composition comprises a powder. In some specific embodiments, a composition comprises crystals. In some specific embodiments, a composition comprises wax.

In some embodiments, a composition is suspended in a gas phase.

In some embodiments, a method comprises grinding plant material.

In some embodiments, a method comprises separating particles of industrial hemp, marijuana, or other plant material by size such as by using a screen, mesh, or particle classifier.

In some embodiments, a cannabinoid molecule, vaporized cannabinoid molecule, or condensed cannabinoid molecule is selected from one or more of THCA, tetrahydrocannabivarin carboxylic acid ("THCVA"), tetrahydrocannabiorcolic acid ("THCOA"), CBDA, CBDVA, cannabidiorcolic acid ("CBDOA"), cannabichromenic acid ("CBCA"), cannabichromevarinic acid ("CBCVA"), cannabigerolic acid ("CBGA"), cannabigerovarinic acid ("CBGVA"), cannabicyclolic acid ("CBLA"), cannabielsoic acid ("CBEA"), perrottetinenic acid, carboxylates of any of the preceding molecules, naturally-occurring ethers of any of the preceding molecules, and stereoisomers of any one of the preceding molecules.

In some embodiments, a cannabinoid molecule, modified cannabinoid molecule, vaporized cannabinoid molecule, or condensed cannabinoid molecule is selected from one or more of THC, tetrahydrocannabivarin ("THCV"), tetrahydrocannabiorcol ("THCO"), CBD, CBDV, cannabidiorcol, ("CBDO"), cannabichromene ("CBC"), cannabichromevarin ("CBCV"), cannabigerol ("CBG"), cannabigerovarin ("CBGV"), cannabicyclol ("CBL"), cannabielsoin ("CBE"), perrottetinene, naturally-occurring ethers of any of the preceding molecules, and stereoisomers of any of the preceding molecules.

In some specific embodiments, a cannabinoid molecule, vaporized cannabinoid molecule, or condensed cannabinoid molecule is CBDA. In some specific embodiments, a cannabinoid molecule, vaporized cannabinoid molecule, or condensed cannabinoid molecule is CBDVA, which is also known as 2,4-dihydroxy-3-[(1R,6R)-6-isopropenyl-3-methylcyclohex-2-en-1-yl]-6-propylbenzoic acid. In some specific embodiments, a cannabinoid molecule, vaporized cannabinoid molecule, or condensed cannabinoid molecule is THCA. In some specific embodiments, a cannabinoid molecule, vaporized cannabinoid molecule, or condensed cannabinoid molecule is THCVA, which is also known as (6aR,10aR)-1-hydroxy-6,6,9-trimethyl-3-propyl-6a,7,8,10a-tetrahydro-6H-benzo[c]chromene-2-carboxylic acid.

In some specific embodiments, a modified cannabinoid molecule, vaporized cannabinoid molecule, or condensed cannabinoid molecule is CBD, which is also known as 2-[(1R,6R)-6-isopropenyl-3-methylcyclohex-2-en-1-yl]-5-pentylbenzene-1,3-diol. In some very specific embodiments, a modified cannabinoid molecule is CBD. In some very specific embodiments, a vaporized cannabinoid molecule is CBD. In some very specific embodiments, a condensed cannabinoid molecule is CBD.

In some specific embodiments, a modified cannabinoid molecule, vaporized cannabinoid molecule, or condensed cannabinoid molecule is CBDV, which is also known as 2-[(1R,6R)-6-isopropenyl-3-methylcyclohex-2-en-1-yl]-5-propylbenzene-1,3-diol. In some very specific embodiments, a modified cannabinoid molecule is CBDV. In some very specific embodiments, a vaporized cannabinoid molecule is CBDV. In some very specific embodiments, a condensed cannabinoid molecule is CBDV.

In some specific embodiments, a modified cannabinoid molecule, vaporized cannabinoid molecule, or condensed cannabinoid molecule is THC, which is also known as (6aR,10aR)-6,6,9-trimethyl-3-pentyl-6a,7,8,10a-tetrahydro-6H-benzo[c]chromen-1-ol. In some very specific embodiments, a modified cannabinoid molecule is THC. In some very specific embodiments, a vaporized cannabinoid molecule is THC. In some very specific embodiments, a condensed cannabinoid molecule is THC.

In some specific embodiments, a modified cannabinoid molecule, vaporized cannabinoid molecule, or condensed cannabinoid molecule is THCV, which is also known as (6aR,10aR)-6,6,9-trimethyl-3-propyl-6a,7,8,10a-tetrahydro-6H-benzo[c]chromen-1-ol. In some very specific embodiments, a modified cannabinoid molecule is THCV. In some very specific embodiments, a vaporized cannabinoid molecule is THCV. In some very specific embodiments, a condensed cannabinoid molecule is THCV.

In some specific embodiments, a modified cannabinoid molecule, vaporized cannabinoid molecule, or condensed cannabinoid molecule is perrottetinene, which is also known as (6aS,10aR)-6,6,9-trimethyl-3-(2-phenylethyl)-6a,7,8,10a-tetrahydro-6H-benzo[c]chromen-1-ol. In some very specific embodiments, a modified cannabinoid molecule is perrottetinene. In some very specific embodiments, a vaporized cannabinoid molecule is perrottetinene. In some very specific embodiments, a condensed cannabinoid molecule is perrottetinene.

In some specific embodiments, a cannabinoid molecule is THCA or THC, a vaporized cannabinoid molecule is THC, and a condensed cannabinoid molecule is THC.

In some specific embodiments, a cannabinoid molecule is THCVA or THCV, a vaporized cannabinoid molecule is THCV, and a condensed cannabinoid molecule is THCV.

In some specific embodiments, a cannabinoid molecule is THCOA or THCO, a vaporized cannabinoid molecule is THCO, and a condensed cannabinoid molecule is THCO.

In some specific embodiments, a cannabinoid molecule is CBDA or CBD, a vaporized cannabinoid molecule is CBD, and a condensed cannabinoid molecule is CBD.

In some specific embodiments, a cannabinoid molecule is CBDVA or CBDV, a vaporized cannabinoid molecule is CBDV, and a condensed cannabinoid molecule is CBDV.

In some specific embodiments, a cannabinoid molecule is CBDOA or CBDO, a vaporized cannabinoid molecule is CBDO, and a condensed cannabinoid molecule is CBDO.

In some specific embodiments, a cannabinoid molecule is CBCA or CBC, a vaporized cannabinoid molecule is CBC, and a condensed cannabinoid molecule is CBC.

In some specific embodiments, a cannabinoid molecule is CBCVA or CBCV, a vaporized cannabinoid molecule is CBCV, and a condensed cannabinoid molecule is CBCV.

In some specific embodiments, a cannabinoid molecule is CBGA or CBG, a vaporized cannabinoid molecule is CBG, and a condensed cannabinoid molecule is CBG.

In some specific embodiments, a cannabinoid molecule is CBGVA or CBGV, a vaporized cannabinoid molecule is CBGV, and a condensed cannabinoid molecule is CBGV.

In some specific embodiments, a cannabinoid molecule is CBLA or CBL, a vaporized cannabinoid molecule is CBL, and a condensed cannabinoid molecule is CBL.

In some specific embodiments, a cannabinoid molecule is CBEA or CBE, a vaporized cannabinoid molecule is CBE, and a condensed cannabinoid molecule is CBE.

In some specific embodiments, a cannabinoid molecule is perrottetinenic acid or perrottetinene, a vaporized cannabinoid molecule is perrottetinene, and a condensed cannabinoid molecule is perrottetinene.

In some embodiments, a composition comprises CBDA, CBDVA, THCA, THCVA, and CBGA at a concentration of at least 6% by weight. In some embodiments, a composition comprises CBDA, CBDVA, THCA, THCVA, and CBGA at a combined concentration of 5% to 30%, 10% to 35%, or 15% to 40% by weight.

In some embodiments, a composition comprises CBDA at a concentration of at least 6% by weight. In some embodiments, a composition comprises CBDA at a concentration of 5% to 30%, 10% to 35%, or 15% to 40% by weight.

In some embodiments, a composition comprises CBDVA at a concentration of at least 0.2% by weight such. In some embodiments, a composition comprises CBDVA at a concentration of 0.1% to 5% by weight, In some embodiments, a composition comprises THCA at a concentration of at least 15% by weight. In some embodiments, a composition comprises THCA at a concentration of 5% to 30%, 10% to 35%, or 15% to 40% by weight.

In some embodiments, a composition comprises THCVA at a concentration of at least 0.2% by weight. In some embodiments, a composition comprises THCVA at a concentration of 0.1% to 5% by weight, In some embodiments, a method comprises suspending a particle of a composition comprising cannabinoids in a gas phase, in which the particle comprises a cannabinoid molecule in a liquid phase or in a solid phase. In some specific embodiments, a composition comprising a cannabinoid molecule in a liquid phase or a solid phase is contacted with sufficient energy to convert the cannabinoid molecule in the liquid phase or the solid phase into a vaporized cannabinoid molecule in a gas phase while a particle of the composition comprising the cannabinoid molecule in the liquid phase or the solid phase is suspended in the gas phase.

In some embodiments, a method comprises suspending a plurality of particles of a composition comprising cannabinoids in a gas phase, in which the plurality of particles comprises a cannabinoid molecule in a liquid phase or in a solid phase. In some specific embodiments, a composition comprising a cannabinoid molecule in a liquid phase or in a solid phase is contacted with sufficient energy to convert the cannabinoid molecule in the liquid phase or the solid phase into a vaporized cannabinoid molecule in a gas phase while a plurality of particles of the composition comprising the cannabinoid molecule in the liquid phase or the solid phase is suspended in the gas phase.

In some embodiments, a method comprises suspending a droplet of a composition comprising cannabinoids in a gas phase, in which the droplet comprises a cannabinoid molecule in a liquid phase or in a solid phase. In some specific embodiments, a composition comprising a cannabinoid molecule in a liquid phase or in a solid phase is contacted with sufficient energy to convert the cannabinoid molecule in the liquid phase or the solid phase into a vaporized cannabinoid molecule in a gas phase while a droplet of the composition comprising the cannabinoid molecule in the liquid phase or the solid phase is suspended in the gas phase.

In some embodiments, a method comprises suspending a plurality of droplets of a composition comprising cannabinoids in a gas phase, in which the plurality of droplets comprises a cannabinoid molecule in a liquid phase or in a solid phase. In some specific embodiments, a composition comprising a cannabinoid molecule in a liquid phase or in a solid phase is contacted with sufficient energy to convert the cannabinoid molecule in the liquid phase or the solid phase into a vaporized cannabinoid molecule in a gas phase while a plurality of droplets of the composition comprising the cannabinoid molecule in the liquid phase or the solid phase is suspended in the gas phase.

In some embodiments, a gas phase comprises water vapor at a concentration of at least 5% by volume. In some embodiments, a gas phase comprises ethanol vapor at a concentration of at least 5% by volume. A percentage of a gas phase by volume, as described in this patent document, is calculated by dividing the partial pressure of a species of gas, such as molecular oxygen, by the total pressure of the gas phase and then multiplying the result by 100%. Solids and liquids lack any percentage by volume of a gas phase by definition. In some embodiments, a gas phase comprises molecular nitrogen, ethanol vapor, water vapor, carbon dioxide, noble gases, cannabinoids, terpenes, terpene alcohols, and terpenoids at a total concentration of at least 95% by volume.

In some embodiments, converting a cannabinoid molecule in a liquid phase or a solid phase into a vaporized cannabinoid molecule in a gas phase comprises contacting a composition comprising the cannabinoid molecule with less than 100 kilojoules ("kJ") of energy per gram of the composition.

In some embodiments, converting a cannabinoid molecule in a liquid phase or a solid phase into a vaporized cannabinoid molecule in a gas phase comprises contacting a composition comprising the cannabinoid molecule with 0.0003 to 0.04 kilowatt hours of energy per gram of the composition. In some very specific embodiments, converting a cannabinoid molecule in a liquid phase or a solid phase into a vaporized cannabinoid molecule in a gas phase comprises contacting a composition comprising the cannabinoid molecule with 2 kilojoules to 50 kilojoules of energy per gram of the composition.

In some embodiments, converting a cannabinoid molecule in a liquid phase or a solid phase into a vaporized cannabinoid molecule in a gas phase comprises contacting a composition comprising the cannabinoid molecule with less than 100 kilowatts ("kW") of power per gram of the composition for less than 60 seconds. In some specific embodiments, converting a cannabinoid molecule in a liquid phase or a solid phase into a vaporized cannabinoid molecule in a gas phase comprises contacting a composition comprising the cannabinoid molecule with 1 kW to 100 kW of power per gram of the composition for 0.2 to 20 seconds.

In some embodiments, a method comprises irradiating a composition, convectively heating a composition, or conductively heating a composition, in which contacting a composition with sufficient energy comprises one or more of irradiating the composition, convectively heating the composition, or conductively heating the composition. Suitable methods of irradiating a composition are described, for example, in PCT Patent Application Publication No. WO 2018/102711 A1, which is incorporated by reference in its entirety. Suitable methods of convectively heating a composition are described, for example, in PCT Patent Application Publication No. WO 2015/049585 A2, which is incorporated by reference in its entirety. Suitable methods of conductively heating a composition are described, for example, in PCT Patent Application Publication No. WO 2016/161420 A1 and WO 2017/192527 A1, each of which is incorporated by reference in its entirety.

In some embodiments, a method comprises contacting a composition with a heated gas. In some specific embodiments, a method comprises contacting a composition with a heated gas having a temperature of 190° C. to 250° C. In some embodiments, a method comprises contacting a composition with a heated surface. In some specific embodiments, a method comprises contacting a composition with a heated surface having a temperature of 190° C. to 250° C.

In some embodiments, a method comprises coating a surface or heated surface with a composition comprising cannabinoids at a surface-area-to-volume ratio of the composition that is greater than 500 per meter prior to converting a cannabinoid molecule in a liquid phase or a solid phase into a vaporized cannabinoid molecule in a gas phase. In some embodiments, a composition is contacted with sufficient energy to convert a cannabinoid molecule in a liquid phase or a solid phase into a vaporized cannabinoid molecule in a gas phase while the composition is coated on a surface or heated surface at a surface-area-to-volume ratio of the composition that is greater than 500 per meter.

In some embodiments, a method comprises directing a composition comprising cannabinoids along a path having a length of at least 4 meters, in which the composition is contacted with sufficient energy to convert a cannabinoid molecule in a liquid phase or a solid phase into a vaporized cannabinoid molecule in a gas phase while the composition is being directed along the path. In some embodiments, a path has a length of 4 meters to 40 meters. Increasing the length of a path increases the probability that a first cannabinoid molecule will interact with either a second cannabinoid molecule or other catalyst with an appropriate orientation to catalyze the decarboxylation of the first cannabinoid molecule.

In some embodiments, a method comprises directing a composition along a path having a length of at least 4 meters at a rate of at least 2 meters per second. Directing a composition along a path of a specific length at a specific rate can control the amount of energy that contacts the composition. In some embodiments, a path comprises one or more surfaces, and a method comprises heating the one or more surfaces to a temperature of 190° C. to 250° C.

In some embodiments, a composition comprises a non-volatile molecule, and a method comprises separating a vaporized cannabinoid molecule in a gas phase from a non-volatile molecule. In some specific embodiments, separating a vaporized cannabinoid molecule in a gas phase from a non-volatile molecule is performed after converting a cannabinoid molecule in a liquid phase or a solid phase into the vaporized cannabinoid molecule in the gas phase. In some specific embodiments, separating a vaporized cannabinoid molecule in a gas phase from a non-volatile molecule is performed prior to contacting the vaporized cannabinoid molecule with a heat sink. In some very specific embodiments, a method comprises separating a vaporized cannabinoid molecule in a gas phase from a non-volatile molecule by directing the gas phase through a cyclone. In some very specific embodiments, a method comprises separating a vaporized cannabinoid molecule in a gas phase from a non-volatile molecule by directing the gas phase through a filter such as an air filter. In some specific embodiments, a method comprises collecting a non-volatile molecule.

In some embodiments, a method converts less than 2% of a cannabinoid molecule of a composition into cannabinol (which is also known as 6,6,9-trimethyl-3-pentyl-benzo[c]chromen-1-ol) by mole. In some very specific embodiments, a method comprises producing a liquid distillate comprising a condensed cannabinoid molecule and cannabinol at a molar ratio greater than 50:1.

In some specific embodiments, a composition comprises CBDA, and a method converts less than 2% of the CBDA of the composition into cannabinol by mole. In some very specific embodiments, a method comprises producing a liquid distillate comprising CBD and cannabinol at a molar ratio greater than 50:1.

In some specific embodiments, a composition comprises THCA, and a method converts less than 2% of the THCA of the composition into cannabinol by mole. In some very specific embodiments, a method comprises producing a liquid distillate comprising THC and cannabinol at a molar ratio greater than 50:1.

In some embodiments, a method converts less than 0.2% of a cannabinoid molecule of a composition into 6,6,9-trimethyl-3-pentyl-6a,7,10,10a-tetrahydro-6H-benzo[c]chromen-1-ol ("Δ8-THC" or "delta-8-tetrahydrocannabinol") by mole. In some very specific embodiments, a method comprises producing a liquid distillate comprising a condensed cannabinoid molecule and Δ8-THC at a molar ratio greater than 500:1.

In some specific embodiments, a composition comprises CBDA, and a method converts less than 2% of the CBDA of the composition into Δ8-THC by mole. In some very specific embodiments, a method comprises producing a liquid distillate comprising CBD and Δ8-THC at a molar ratio greater than 500:1.

In some specific embodiments, a composition comprises THCA, and a method converts less than 2% of the THCA of the composition into Δ8-THC by mole. In some very specific embodiments, a method comprises producing a liquid distillate comprising THC and Δ8-THC at a molar ratio greater than 500:1.

In some embodiments, a heat sink has a surface area greater than 10% of the surface area of a composition comprising cannabinoids. A heat sink having a relatively large surface area allows for rapid condensation. In some specific embodiments, a heat sink is a colloid comprising a gas-phase dispersion medium. In some very specific embodiments, a heat sink is an aerosol or a foam. In some very specific embodiments, a heat sink is a spray. Colloids such as aerosols and foams generally have large surface areas, and colloids are therefore suitable heat sinks.

In some embodiments, a heat sink comprises a volatile liquid. Heat sinks comprising a volatile liquid are particularly useful because the vaporization of a volatile liquid can absorb a large amount of energy. In some specific embodiments, a heat sink comprises a volatile liquid, and the volatile liquid comprises one or both of ethanol and water. In some very specific embodiments, a heat sink comprises a volatile liquid, and the volatile liquid comprises ethanol and water at a combined concentration by weight of at least 90%.

In some embodiments, contacting a vaporized cannabinoid molecule with a heat sink comprises passive cooling such as by exposing the vaporized cannabinoid molecule or a container comprising the vaporized cannabinoid molecule to ambient temperature. In some specific embodiments, exposing a vaporized cannabinoid molecule or a container comprising the vaporized cannabinoid molecule to ambient temperature comprises cooling in an autoclave. In some specific embodiments, exposing a vaporized cannabinoid molecule to ambient temperature comprises directing the vaporized cannabinoid molecule through a fluid-cooled condenser.

In some embodiments, a method comprises contacting a vaporized cannabinoid molecule with a heat sink less than 20 seconds after converting a cannabinoid molecule in a liquid phase or a solid phase into the vaporized cannabinoid molecule in a gas phase.

In some embodiments, a method comprises condensing a vaporized cannabinoid molecule into a condensed cannabinoid molecule less than 20 seconds after converting a cannabinoid molecule in a liquid phase or a solid phase into the vaporized cannabinoid molecule in a gas phase. In some specific embodiments, a method comprises condensing a modified cannabinoid molecule into a condensed cannabinoid molecule less than 60 seconds after contacting a composition with sufficient energy to convert a native cannabinoid molecule into (i) a carbon dioxide molecule and (ii) the modified cannabinoid molecule in a gas phase. Cannabinoid vapor can be converted into condensed cannabinoids about 2 seconds after vaporization with excellent yields of decarboxylated cannabinoids when a composition comprising cannabinoids is a plant material having a surface-area-to-volume ratio and water content as described in this patent document.

In some specific embodiments, a method comprises producing a liquid distillate comprising cannabinol at a concentration less than 0.8% by weight. In some very specific embodiments, a method comprises producing a liquid distillate comprising one or both of CBD and THC at a concentration greater than 6% by weight and cannabinol at a concentration less than 0.8% by weight.

In some embodiments, a method comprises converting at least 95% of a cannabinoid molecule of a composition into a vaporized cannabinoid molecule in a gas phase by mole. In some specific embodiments, a method comprises converting at least 75% of a native cannabinoid molecule into a condensed cannabinoid molecule per mole. In some embodiments, a method comprises producing a liquid distillate comprising cannabinoids, and less than 2% of the cannabinoids of the liquid distillate comprise a carboxyl group.

In some embodiments, a method comprises producing a liquid distillate comprising condensed cannabinoid molecules selected from one, two, three, four, or each of CBD, CBDV, THC, THCV, and CBG. In some specific embodiments, a method comprises producing a liquid distillate comprising condensed cannabinoid molecules in which at least 95% of the condensed cannabinoid molecules of the liquid distillate are CBD, CBDV, THC, THCV, and CBG by weight.

In some embodiments, a method comprises producing a liquid distillate comprising ethanol. In some specific embodiments, a method comprises producing a liquid distillate comprising water and ethanol at a combined concentration of at least 50% by weight. Ethanol reduces the viscosity of a liquid distillate which allows for improved automation of the purification methods.

In some embodiments, a liquid distillate comprises a non-cannabinoid molecule and a condensed cannabinoid molecule, and a method comprises separating the non-cannabinoid molecule from the condensed cannabinoid molecule to produce a product. In some embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of at least 60% by weight. In some embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of 55% to 65%, 60% to 70%, 65% to 75%, 70% to 80%, 75% to 85%, 80% to 90%, 85% to 95%, or 90% to 99.9% by weight.

In some embodiments, a liquid distillate comprises a non-cannabinoid molecule and CBD, and a method comprises separating the non-cannabinoid molecule from the CBD to produce a product comprising the CBD at a concentration of at least 60% by weight. In some embodiments, a liquid distillate comprises a non-cannabinoid molecule and CBD, and a method comprises separating the non-cannabinoid molecule from the CBD to produce a product comprising the CBD at a concentration of 55% to 65%, 60% to 70%, 65% to 75%, 70% to 80%, 75% to 85%, 80% to 90%, 85% to 95%, or 90% to 99.9% by weight.

In some embodiments, a liquid distillate comprises a non-cannabinoid molecule and CBDV, and a method comprises separating the non-cannabinoid molecule from the CBDV to produce a product comprising the CBDV at a concentration of at least 0.2% by weight. In some embodiments, a liquid distillate comprises a non-cannabinoid molecule and CBDV, and a method comprises separating the non-cannabinoid molecule from the CBDV to produce a product comprising the CBDV at a concentration of 0.1% to 10% by weight.

In some embodiments, a liquid distillate comprises a non-cannabinoid molecule, CBD, and CBDV, and a method comprises separating the non-cannabinoid molecule from the CBD and CBDV to produce a product comprising the CBD and CBDV at a combined concentration of at least 60% by weight. In some embodiments, a liquid distillate comprises a non-cannabinoid molecule, CBD, and CBDV, and a method comprises separating the non-cannabinoid molecule from the CBD and CBDV to produce a product comprising the CBD and CBDV at a combined concentration of 55% to 65%, 60% to 70%, 65% to 75%, 70% to 80%, 75% to 85%, 80% to 90%, 85% to 95%, or 90% to 99.9% by weight.

In some embodiments, a liquid distillate comprises a non-cannabinoid molecule and THC, and a method comprises separating the non-cannabinoid molecule from the THC to produce a product comprising the THC at a concentration of at least 60% by weight. In some embodiments, a liquid distillate comprises a non-cannabinoid molecule and THC, and a method comprises separating the non-cannabinoid molecule from the THC to produce a product comprising the THC at a concentration of 55% to 65%, 60% to 70%, 65% to 75%, 70% to 80%, 75% to 85%, 80% to 90%, 85% to 95%, or 90% to 99.9% by weight.

In some embodiments, a liquid distillate comprises a non-cannabinoid molecule and THCV, and a method comprises separating the non-cannabinoid molecule from the THCV to produce a product comprising the THCV at a concentration of at least 0.2% by weight. In some embodiments, a liquid distillate comprises a non-cannabinoid molecule and THCV, and a method comprises separating the non-cannabinoid molecule from the THCV to produce a product comprising the THCV at a concentration of 0.1% to 10% by weight.

In some embodiments, a liquid distillate comprises a non-cannabinoid molecule, THC, and THCV, and a method comprises separating the non-cannabinoid molecule from the THC and THCV to produce a product comprising the THC and THCV at a combined concentration of at least 60% by weight. In some embodiments, a liquid distillate comprises a non-cannabinoid molecule, THC, and THCV, and a method comprises separating the non-cannabinoid molecule from the THC and THCV to produce a product comprising the THC and THCV at a combined concentration of 55% to 65%, 60% to 70%, 65% to 75%, 70% to 80%, 75% to 85%, 80% to 90%, 85% to 95%, or 90% to 99.9% by weight.

In some embodiments, a method comprises producing a product comprising cannabinoids at a concentration of at least 50% by weight. In some embodiments, a method comprises producing a product comprising a condensed cannabinoid molecule at a concentration of at least 50% by weight. In some specific embodiments, a method comprises producing a product comprising one, two, three, four, or each of CBD, CBDV, THC, THCV, and CBG at a combined concentration of at least 50% by weight.

In some embodiments, a composition comprises a volatile non-cannabinoid molecule, and a method comprises separating the volatile non-cannabinoid molecule from a condensed cannabinoid molecule. In some specific embodiments, a composition comprises a volatile non-cannabinoid molecule, and a method comprises (i) separating the volatile non-cannabinoid molecule from a condensed cannabinoid molecule, and then (ii) collecting the volatile non-cannabinoid molecule. In some specific embodiments, a volatile non-cannabinoid molecule is water. In some specific embodiments, a volatile non-cannabinoid molecule is ethanol. In some specific embodiments, a volatile non-cannabinoid molecule is a terpene, terpene alcohol, or terpenoid. In some very specific embodiments, a volatile non-cannabinoid molecule is selected from one or more of the terpenes beta-caryophyllene, humulene, myrcene, limonene, alpha-terpinene, delta-3-carene, and terpinolene; the terpene alcohols (−)-guaiol, (−)-alpha-bisabolol, linalool, alpha-terpineol, nerolidol, borneol, and (−)-isopulegol; the terpenoids caryophyllene oxide and eucalyptol; and the terpene oxidation product para-cymene. In some very specific embodiments, a method comprises separating a volatile non-cannabinoid molecule from a condensed cannabinoid molecule using a rotary evaporator, falling film evaporator, short-path distillation apparatus, retort, or distillation still.

Prior art methods are generally incapable of decarboxylating cannabinoids in the presence of terpenes, terpene alcohols, and terpenoids and then recovering the terpenes, terpene alcohols, and terpenoids because prolonged heating during traditional decarboxylation, such as in a vacuum oven, either vaporizes and discards the terpenes, terpene alcohols, and terpenoids, thermally degrades the terpenes, terpene alcohols, and terpenoids, or both degrades and discards the terpenes, terpene alcohols, and terpenoids. Decarboxylation also results in the production of carbon dioxide, which increases the pressure of a closed vessel and limits the ability to separate cannabinoid carboxylic acids from terpenes, terpene alcohols, and terpenoids by distillation. Short-path distillation apparatuses capable of separating cannabinoids from terpenes, terpene alcohols, and terpenoids often comprise glass (see, for example, Short Path Distillation Plant VKL 70-5, ROOT SCIENCES, Washington, US), and the rapid increase in pressure caused by purifying a composition comprising a cannabinoid carboxylic acid in such an apparatus risks breaking the glass or otherwise damaging the apparatus.

The methods disclosed in this patent document are capable of distilling terpenes, terpene alcohols, and terpenoids directly from cannabis while both co-distilling and decarboxylating cannabinoids from the cannabis, which produces a novel liquid distillate comprising both decarboxylated cannabinoids and terpenes, terpene alcohols, and terpenoids. Prior art methods of preparing commercial products comprising decarboxylated cannabinoids and terpenes, terpene alcohols, or terpenoids from cannabis at (i) terpene, terpene alcohol, and terpenoid to (ii) decarboxylated cannabinoid ratios exceeding 1:100 require the combination of decarboxylated cannabinoids obtained from cannabis with exogenous terpenes, terpene alcohols, or terpenoids after decarboxylating the cannabinoids. One of the unexpected implications of the methods disclosed in this patent document is that, in addition to the production of high-value decarboxylated cannabinoids from cannabis, the methods also allow the co-production of high-value terpenes, terpene alcohols, and terpenoids from cannabis.

Various aspects of the disclosure relate to a carboxylate ester of a cannabinoid molecule and a hydrophilic molecule, which is also referred to as a cannabinoid ester in this patent document.

In some embodiments, a method comprises converting a cannabinoid molecule into a carboxylate ester of the cannabinoid molecule and a hydrophilic molecule. In some specific embodiments, a method comprises converting a cannabinoid molecule that lacks a carboxyl group into a carboxylate ester of the cannabinoid molecule and a hydrophilic molecule. In some very specific embodiments, a method comprises converting a condensed cannabinoid molecule as described in this patent document into a carboxylate ester of the condensed cannabinoid molecule and a hydrophilic molecule.

In some embodiments, a cannabinoid molecule such as a condensed cannabinoid molecule has a solubility in water of less than 100 mg per liter, 50 mg per liter, 25 mg per liter, 10 mg per liter, 5 mg per liter, 2 mg per liter, or 1 mg per liter, and a cannabinoid ester of the cannabinoid molecule and a hydrophilic molecule has a solubility in water of greater than 100 mg per liter, 50 mg per liter, 25 mg per liter, 10 mg per liter, 5 mg per liter, 2 mg per liter, or 1 mg per liter, respectively.

In some embodiments, an aqueous composition comprises a cannabinoid ester dissolved in water at a concentration greater than 1 mg per liter, 2 mg per liter, 5 mg per liter, 10 mg per liter, 25 mg per liter, 50 mg per liter, or 100 mg per liter.

In some specific embodiments, a condensed cannabinoid molecule comprises a hydroxyl group, and the hydroxyl group comprises an oxygen atom. In some specific embodiments, a hydrophilic molecule comprises a carboxyl group, and the carboxyl group comprises a carbon atom. In some specific embodiments, an oxygen atom of a hydroxyl group of a cannabinoid molecule forms an ester bond with a carbon atom of a carboxyl group of a hydrophilic molecule in a cannabinoid ester.

In some embodiments, a method comprises (i) providing a cannabinoid molecule, in which the cannabinoid molecule comprises a hydroxyl group, the hydroxyl group is covalently bound to a first carbon atom, and the cannabinoid molecule lacks a carboxyl group; (ii) providing a hydrophilic molecule, in which the hydrophilic molecule comprises two ionizable functional groups, the two ionizable functional groups comprise a carboxyl group, and the carboxyl group comprises a second carbon atom; and (iii) forming a carboxylate ester between the cannabinoid molecule and the hydrophilic molecule, in which the first carbon atom forms a covalent bond with an oxygen atom in the carboxylate ester, and the oxygen atom forms a covalent bond with the second carbon atom in the carboxylate ester.

In some embodiments, a cannabinoid ester comprises a cannabinoid molecule and a hydrophilic molecule; the cannabinoid molecule comprises a hydroxyl group, and the hydroxyl group is covalently bound to a first carbon atom; the hydrophilic molecule comprises a carboxyl group, and the carboxyl group comprises a second carbon atom; the first carbon atom forms a covalent bond with an oxygen atom in the cannabinoid ester; and the oxygen atom forms a covalent bond with the second carbon atom in the cannabinoid ester.

In some specific embodiments, a hydrophilic molecule is selected from citric acid, fumaric acid, malic acid, maleic acid, aconitic acid, gluconic acid, malonic acid, succinic acid, glutaric acid, adipic acid, azelaic acid, tartaric acid, a deprotonated form of any one of the preceding molecules, or a stereoisomer of any one of the preceding molecules. In some specific embodiments, a hydrophilic molecule is selected from aspartic acid, glutamic acid, lysine, arginine, histidine, serine, threonine, asparagine, glutamine, glycine, a protonated or deprotonated form of any one of the preceding molecules, or a stereoisomer of any one of the preceding molecules.

In some specific embodiments, a cannabinoid molecule of a cannabinoid ester is selected from CBD, CBDV, CBDO, CBG, CBGV, CBL, CBE, THC, THCV, THCO, and perrottetinene, a naturally-occurring ether of any one of CBD, CBDV, CBDO, CBG, and CBGV, and a stereoisomer of any one of the preceding molecules.

Various combinations of the features disclosed in this patent document will be evident to those of ordinary skill, and these combinations are expressly contemplated by the inventors. This patent document discloses each linguistic and grammatical combination of different features disclosed anywhere in the patent document as though any specific combination were disclosed in the same sentence. The language and grammar of this patent document is intentionally selected to explicitly clarify the combinations contemplated by the inventors such that, for example, embodiments related to methods of producing a cannabinoid ester are combinable with methods of purifying a cannabinoid molecule.

The words "comprising," "comprises," and "comprise" refer to open-ended sets. For example, a composition comprising water can also comprise ethanol.

The phrases "consisting of," "consists of," and "consist of" refer to closed sets. For example, a composition consisting of water cannot also comprise ethanol.

Each instance of the words "comprising," "comprises," and "comprise" in this patent document may be substituted with the phrases "consisting of," "consists of," and "consist of," respectively.

The phrases "consisting essentially of," "consists essentially of," and "consist essentially of" refer to closed sets that optionally contain one or more undisclosed elements that do not materially affect the nature of any given closed set. For example, a composition consisting essentially of water can comprise a trace amount of ethanol so long as the trace amount of ethanol does not materially affect the nature of the composition in the context of this patent document.

Each instance of the words "comprising," "comprises," and "comprise" in this patent document may be substituted with the phrases "consisting essentially of," "consists essentially of," and "consist essentially of," respectively.

Each instance of the phrases "consisting of," "consists of," and "consist of" in this patent document may be substituted with the phrases "consisting essentially of," "consists essentially of," and "consist essentially of," respectively.

The following examples provide a framework to implement certain aspects of the disclosure in commercially-viable processes, and these examples do not limit the scope of this patent document or any claim that matures from the disclosure of this patent document.

EXEMPLIFICATION

Figure 3:
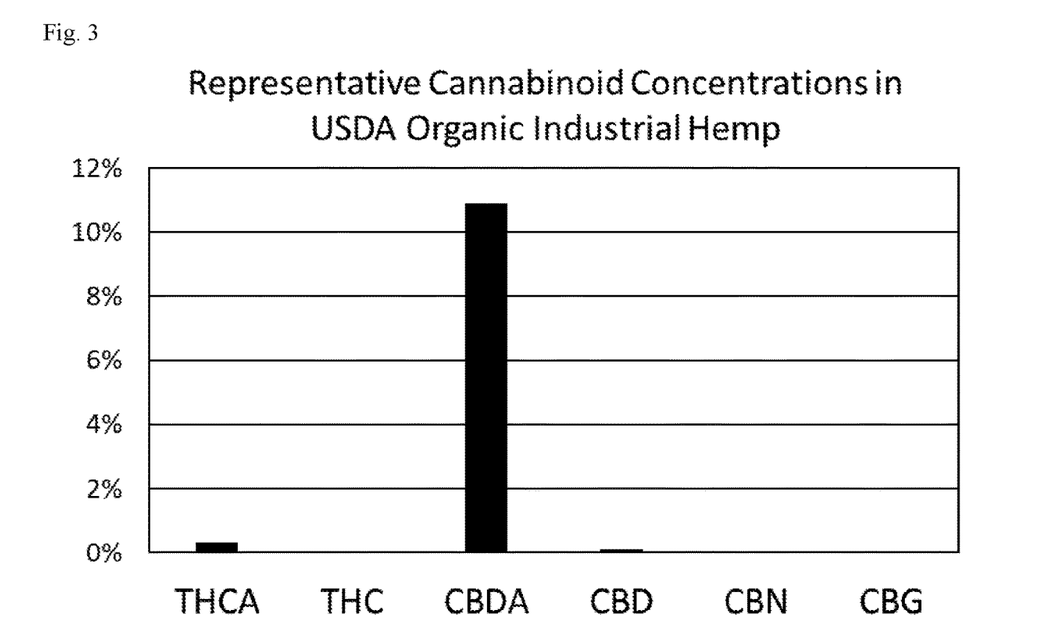
FIG. 3 is a bar graph depicting the THCA, THC, CBDA, CBD, CBN, and CBG concentrations found in a typical sample of USDA organic industrial hemp.

Example 1. Decarboxylation and Distillation of Cannabinoids from Organic Industrial Hemp Example 1 is prophetic and representative of actual methods. The method of PCT Patent Application Publication No. WO 2016/161420 A1 is performed using organic industrial hemp. The water content of the hemp is less than 10% by weight. The cannabinoid content of the hemp is about 11-12% by weight and consists of about 11% CBDA, 0.1% CBD, 0.3% THCA, and 0% THC by weight (see, for example, FIG. 3). The hemp is ground and sifted to provide a particulate having an average diameter less than 2 mm and a surface-area-to-volume ratio greater than 3000 per meter. The hemp is suspended in heated gas to vaporize the cannabinoids. The heated gas is produced by resistive heating at 10-20 kW. The oxygen content of the heated gas is significantly below the ~20% oxygen content of air by volume. Oxygen is reduced relative to air by blanketing the distillation machine in an inert gas and by evaporating water from the hemp. The heated gas and suspended hemp are directed through heated tubes having a length of 5 to 50 meters at a rate of 5 to 20 meters per second. A known mass of hemp is directed through the heated tubes at a known rate such that the hemp is exposed to less than 100 kJ of energy per gram of the hemp. The heated tubes reverse direction in Cartesian space several times to increase the number of collisions between particles and gas-phase molecules. Cannabinoid vapor is mechanically separated from suspended non-volatile molecules of the hemp using a cyclone and filters. Cannabinoid vapor is condensed approximately 1 to 5 seconds after vaporization. A liquid distillate is collected by rinsing the condensed cannabinoids from the surfaces of the heat sink with ethanol. Greater than 90% of the cannabinoids of the hemp are recovered as cannabinoids of the liquid distillate by mole. Greater than 95% of the cannabinoids of the liquid distillate are decarboxylated. A rotary evaporator is used to remove ethanol and water from the liquid distillate to produce a uniform product comprising at least 10% by weight cannabinoids.

Figure 4:
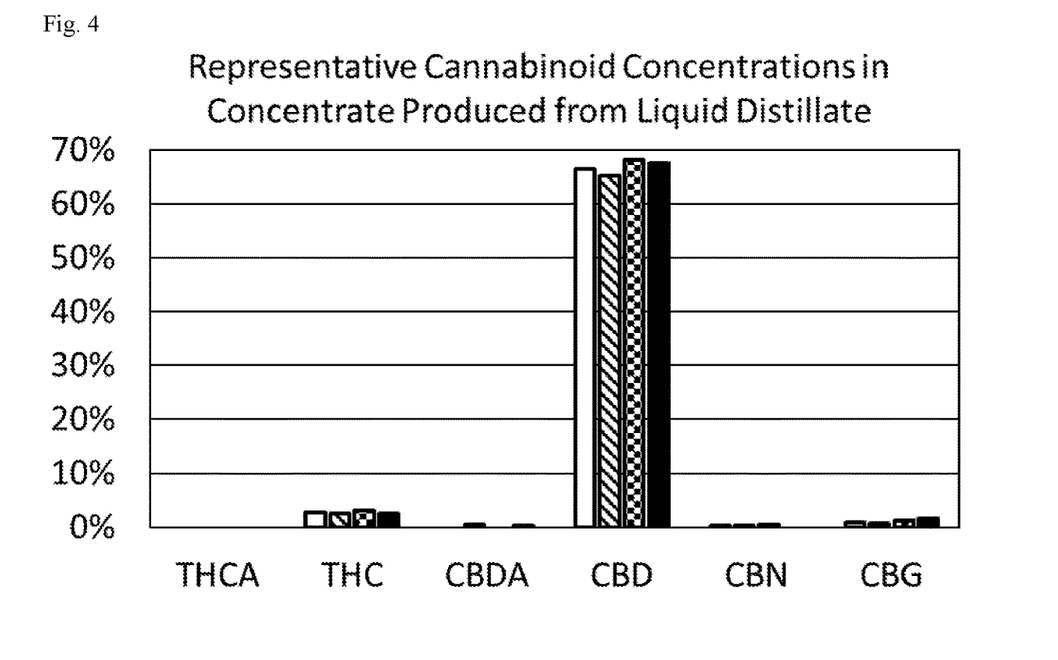
FIG. 4 is a bar graph depicting the THCA, THC, CBDA, CBD, CBN, and CBG concentrations found in four different concentrate products produced according to methods disclosed in this patent document.

Example 2. Products Produced by Decarboxylation and Distillation of Cannabinoids from Organic Industrial Hemp The method of Example 1 was performed on four different batches of organic hemp, and cannabinoid concentrations of concentrated products produced from the liquid distillates were determined by an accredited, third-party cannabis testing laboratory. Actual cannabinoid concentrations by weight of concentrated products produced from liquid distillates are shown in FIG. 4 and Table 1. In each instance, greater than 99.5% of the cannabinoids of the concentrated products were decarboxylated.

TABLE 1

Actual Concentrations of Cannabinoids in Four Concentrated Products Produced from Liquid Distillate Following Decarboxylation and Distillation of the Cannabinoids from Organic Industrial Hemp

|  | 1 | 2 | 3 | 4 |
| --- | --- | --- | --- | --- |
| CBD | 66.5% | 65.2% | 68.1% | 67.6% |
| CBDA | 0.0% | 0.6% | 0.0% | 0.3% |
| THC | 2.7% | 2.6% | 3.2% | 2.6% |
| THCA | 0.0% | 0.0% | 0.0% | 0.0% |
| CBN | 0.4% | 0.3% | 0.4% | 0.0% |
| CBG | 0.96% | 0.76% | 1.27% | 1.62% |

Figure 5:
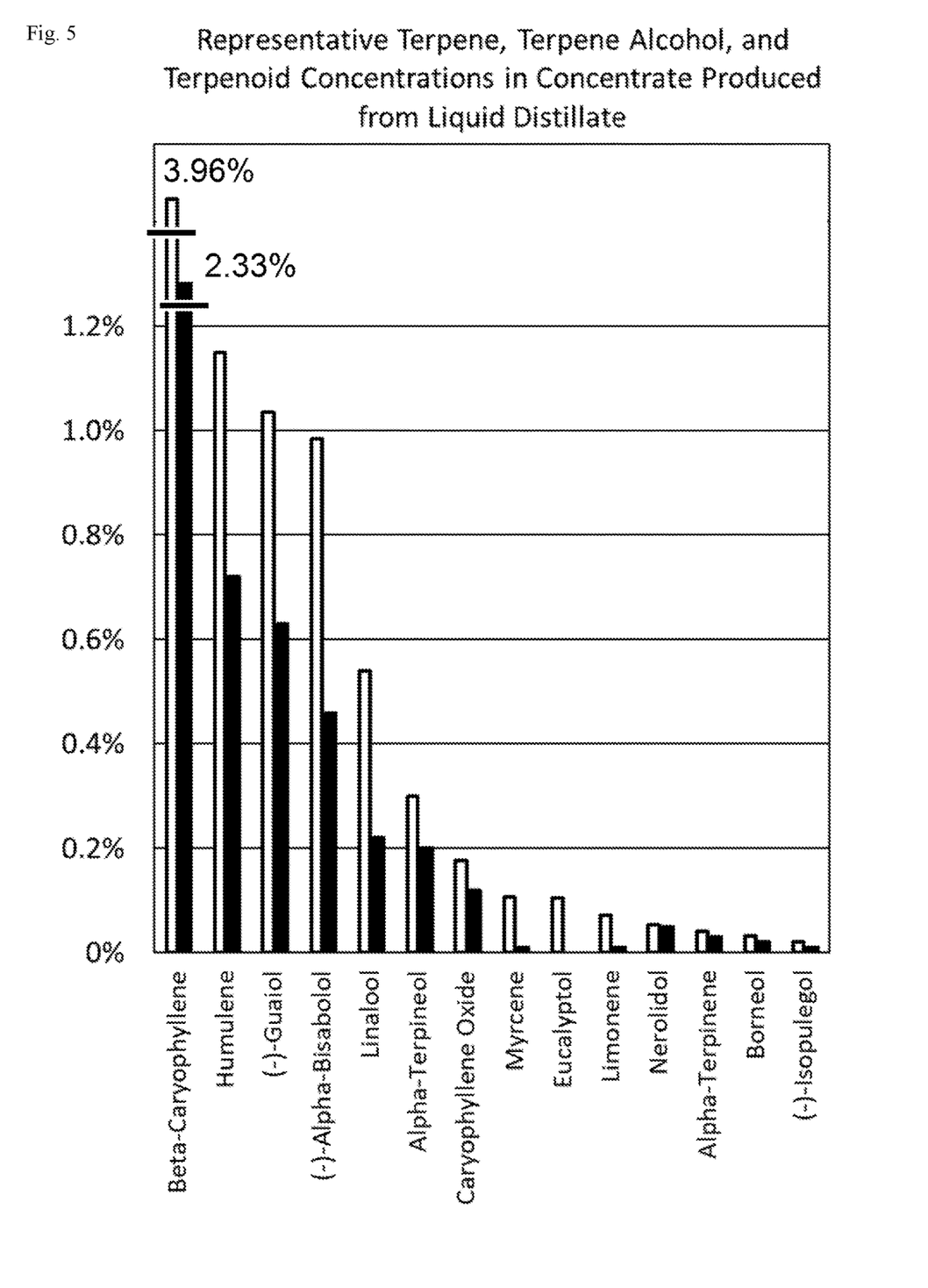
FIG. 5 is a bar graph depicting terpene, terpene alcohol, and terpenoid concentrations found in two different concentrate products produced according to methods disclosed in this patent document.

Example 3. Co-Distillation of Cannabinoids, Terpenes, Terpene Alcohols, and Terpenoids from Organic Industrial Hemp The method of Example 1 was performed on two different batches of organic hemp to produce two liquid distillates, which were then processed to produce two concentrated products. Terpene, terpene alcohol, and terpenoid concentrations of the two concentrated products were determined by an accredited, third-party cannabis testing laboratory. Actual terpene, terpene alcohol, and terpenoid concentrations by weight are shown in FIG. 5 and Table 2. Approximately 8.7% of a first concentrated product consisted of terpenes, terpene alcohols, and terpenoids by weight, and approximately 5.0% of a second concentrated product consisted of terpenes, terpene alcohols, and terpenoids by weight.

TABLE 2

Actual Concentrations of Terpene, Terpene Alcohols, and Terpenoids in Two Concentrated Products Produced from Liquid Distillates Following Co-distillation of Terpene, Terpene Alcohols, and Terpenoids with Cannabinoids from Organic Industrial Hemp

| Molecule | Concentration by Weight (parts per million) | | Boiling Point | Molecule Type |
| --- | --- | --- | --- | --- |
|  | 1 | 2 |  |  |
| Beta-Caryophyllene | 39,574 | 23,348 | 263° F. | Terpene |
| Humulene | 11,485 | 72,40 | 224° F. | Terpene |
| (−)-Guaiol | 10,351 | 6,390 | 273° F. | Terpene Alcohol |
| (−)-Alpha-Bisabolol | 9,840 | 4,653 | 307° F. | Terpene Alcohol |
| Linalool | 5,400 | 2,222 | 199° F. | Terpene Alcohol |
| Alpha-Terpineol | 2,998 | 2,032 | 420° F. | Terpene Alcohol |
| Caryophyllene Oxide | 1,765 | 1,291 | 536° F. | Terpenoid |
| Myrcene | 1,070 | 176 | 167° F. | Terpene |
| Eucalyptol | 1,058 | ND* | 177° F. | Terpenoid |
| Limonene | 718 | 197 | 176° F. | Terpene |
| Nerolidol | 532 | 547 | 252° F. | Terpene Alcohol |
| Alpha-Terpinene | 414 | 340 | 174° F. | Terpene |
| Borneol | 310 | 218 | 213° F. | Terpene Alcohol |
| (−)-Isopulegol | 206 | 170 | 413° F. | Terpene Alcohol |
| Delta-3-Carene | ND* | 356 | 338° F. | Terpene |
| Para-Cymene | ND* | 205 | 351° F. | Terpene Oxidation Product |
| Terpinolene | ND* | 185 | 369° F. | Terpene |

*ND indicates that a given terpene, terpene alcohol, terpenoid, or terpene oxidation product was not detected at a concentration above the detection limit for the terpene Example 4. Decarboxylation and Distillation of Cannabinoids from Organic Cannabis Example 4 is prophetic and representative of actual methods. The method of PCT Patent Application Publication No. WO 2016/161420 A1 is performed using organic cannabis. The water content of the cannabis is less than 10% by weight. The cannabinoid content of the cannabis is about 20-30% by weight. The cannabis is ground and sifted to provide a particulate having an average diameter less than 2 mm and a surface-area-to-volume ratio greater than 3000 per meter. The cannabis is suspended in heated gas to vaporize the cannabinoids. The heated gas is produced by resistive heating at 10-20 kW. The oxygen content of the heated gas is significantly below the ~20% oxygen content of air by volume. Oxygen is reduced relative to air by blanketing the distillation machine in an inert gas and by evaporating water from the cannabis. The heated gas and suspended cannabis are directed through heated tubes having a length of 5 to 50 meters at a rate of 5 to 20 meters per second. A known mass of cannabis is directed through the heated tubes at a known rate such that the cannabis is exposed to less than 100 kJ of energy per gram of the cannabis. The heated tubes reverse direction in Cartesian space several times to increase the number of collisions between particles and gas-phase molecules. Cannabinoid vapor is mechanically separated from suspended non-volatile molecules of the cannabis using a cyclone and filters. Cannabinoid vapor is condensed approximately 1 to 5 seconds after vaporization. A liquid distillate is collected by rinsing the condensed cannabinoids from the surfaces of the heat sink with ethanol. Greater than 90% of the cannabinoids of the cannabis are recovered as cannabinoids of the liquid distillate by mole. Greater than 95% of the cannabinoids of the liquid distillate are decarboxylated. A rotary evaporator is used to remove ethanol and water from the liquid distillate to produce a uniform product comprising at least 10% by weight cannabinoids.

What is claimed is:

1. A method to purify a cannabinoid molecule from a non-volatile molecule, comprising:
   providing a composition comprising a cannabinoid molecule and a non-volatile molecule, in which both the cannabinoid molecule and the non-volatile molecule are in a liquid phase or a solid phase;
   contacting the composition with energy at a rate of less than 100 kilowatts ("kW") of power per gram of the composition for a duration of less than 60 seconds to convert the cannabinoid molecule in the liquid phase or the solid phase into a vaporized cannabinoid molecule in a gas phase without vaporizing the non-volatile molecule;
   separating the vaporized cannabinoid molecule in the gas phase from the non-volatile molecule;
   contacting the vaporized cannabinoid molecule with a heat sink to condense the vaporized cannabinoid molecule into a condensed cannabinoid molecule in a liquid distillate; and
   collecting the liquid distillate.

2. A method to purify a cannabinoid molecule from a non-volatile molecule, comprising:
   providing a composition comprising a cannabinoid molecule and a non-volatile molecule, in which both the cannabinoid molecule and the non-volatile molecule are in a liquid phase or a solid phase;
   contacting the composition with energy to convert the cannabinoid molecule in the liquid phase or the solid phase into a vaporized cannabinoid molecule in a gas phase without vaporizing the non-volatile molecule;
   separating the vaporized cannabinoid molecule in the gas phase from the non-volatile molecule;
   contacting the vaporized cannabinoid molecule with a heat sink to condense the vaporized cannabinoid molecule into a condensed cannabinoid molecule in a liquid distillate comprising the condensed cannabinoid molecule and cannabinol at a molar ratio greater than 100:1; and
   collecting the liquid distillate.

3. A method to purify a cannabinoid molecule from a non-volatile molecule, comprising:
   providing a composition comprising a cannabinoid molecule and a non-volatile molecule, in which both the cannabinoid molecule and the non-volatile molecule are in a liquid phase or a solid phase;
   contacting the composition with energy to convert the cannabinoid molecule in the liquid phase or the solid phase into a vaporized cannabinoid molecule in a gas phase without vaporizing the non-volatile molecule;
   separating the vaporized cannabinoid molecule in the gas phase from the non-volatile molecule;
   contacting the vaporized cannabinoid molecule with a heat sink to condense the vaporized cannabinoid molecule into a condensed cannabinoid molecule in a liquid distillate, in which the method converts at least 95% of the cannabinoid molecule into the condensed cannabinoid molecule in the liquid distillate by mole; and
   collecting the liquid distillate.

4. The method of claim 1, A method to purify a cannabinoid molecule from a non-volatile molecule, comprising:
   providing a composition comprising a cannabinoid molecule and a non-volatile molecule, in which both the cannabinoid molecule and the non-volatile molecule are in a liquid phase or a solid phase;
   contacting the composition with energy to convert the cannabinoid molecule in the liquid phase or the solid phase into a vaporized cannabinoid molecule in a gas phase without vaporizing the non-volatile molecule;
   separating the vaporized cannabinoid molecule in the gas phase from the non-volatile molecule;
   contacting the vaporized cannabinoid molecule with a heat sink to condense the vaporized cannabinoid molecule into a condensed cannabinoid molecule in a liquid distillate, in which the vaporized cannabinoid molecule is condensed into the condensed cannabinoid molecule less than 30 seconds after the cannabinoid molecule is converted into a vaporized cannabinoid molecule in the gas phase; and
   collecting the liquid distillate.

5. The method of claim 4, in which all of (i) contacting the composition with the energy, (ii) separating the vaporized cannabinoid molecule in the gas phase from the non-volatile molecule, and (iii) contacting the vaporized cannabinoid molecule with the heat sink are performed in a total time of less than 30 seconds.

6. The method of claim 1, comprising A method to purify a cannabinoid molecule from a non-volatile molecule, comprising:
   providing a composition comprising a cannabinoid molecule and a non-volatile molecule, in which both the cannabinoid molecule and the non-volatile molecule are in a liquid phase or a solid phase;
   suspending a particle or a droplet of the composition in a gas phase, in which the particle or droplet comprises the cannabinoid molecule;
   contacting the cannabinoid molecule with energy while the particle or droplet is suspended in the gas phase to convert the cannabinoid molecule in the liquid phase or the solid phase into a vaporized cannabinoid molecule in the gas phase without vaporizing the non-volatile molecule;
   separating the vaporized cannabinoid molecule in the gas phase from the non-volatile molecule;
   contacting the vaporized cannabinoid molecule with a heat sink to condense the vaporized cannabinoid molecule into a condensed cannabinoid molecule in a liquid distillate; and
   collecting the liquid distillate.

7. A method to purify a cannabinoid molecule from a non-volatile molecule, comprising:
   providing a composition comprising a cannabinoid molecule and a non-volatile molecule, in which both the cannabinoid molecule and the non-volatile molecule are in a liquid phase or a solid phase;
   coating a heated surface with the composition at a surface-area-to-volume ratio of the composition that is greater than 500 per meter ($m^{-1}$);
   contacting the composition with energy when the heated surface is coated with the composition to convert the cannabinoid molecule in the liquid phase or the solid phase into a vaporized cannabinoid molecule in a gas phase without vaporizing the non-volatile molecule;

separating the vaporized cannabinoid molecule in the gas phase from the non-volatile molecule;

contacting the vaporized cannabinoid molecule with a heat sink to condense the vaporized cannabinoid molecule into a condensed cannabinoid molecule in a liquid distillate; and collecting the liquid distillate.

8. A method to purify a cannabinoid molecule from a non-volatile molecule, comprising:

providing a composition comprising a cannabinoid molecule and a non-volatile molecule, in which both the cannabinoid molecule and the non-volatile molecule are in a liquid phase or a solid phase;

directing the composition along a heated path having a length of at least 4 meters;

contacting the composition with energy in the heated path to convert the cannabinoid molecule in the liquid phase or the solid phase into a vaporized cannabinoid molecule in a gas phase without vaporizing the non-volatile molecule;

separating the vaporized cannabinoid molecule in the gas phase from the non-volatile molecule;

contacting the vaporized cannabinoid molecule with a heat sink to condense the vaporized cannabinoid molecule into a condensed cannabinoid molecule in a liquid distillate; and collecting the liquid distillate.

9. A method to purify a cannabinoid molecule from a non-volatile molecule, comprising:

providing a composition comprising a cannabinoid molecule and a non-volatile molecule, in which both the cannabinoid molecule and the non-volatile molecule are in a liquid phase or a solid phase;

grinding the composition to a surface-area-to-volume ratio greater than 500 per meter;

contacting the composition with energy to convert the cannabinoid molecule in the liquid phase or the solid phase into a vaporized cannabinoid molecule in a gas phase without vaporizing the non-volatile molecule;

separating the vaporized cannabinoid molecule in the gas phase from the non-volatile molecule;

contacting the vaporized cannabinoid molecule with a heat sink to condense the vaporized cannabinoid molecule into a condensed cannabinoid molecule in a liquid distillate; and collecting the liquid distillate.

10. The method of claim 6, comprising:

grinding the composition to a surface-area-to-volume ratio greater than 500 per meter to produce particles of the composition; and suspending the particles of the composition in the gas phase;

in which:

the particles of the composition comprise the cannabinoid molecule; and the cannabinoid molecule is contacted with the energy while the particles of the composition are suspended in the gas phase.

11. The method of claim 6, comprising:

suspending particles of the composition in the gas phase; and directing the particles of the composition along a heated path having a length of at least 4 meters;

in which:

the particles of the composition comprise the cannabinoid molecule; and the cannabinoid molecule is contacted with the energy in the heated path.

12. A method to chemically-modify a cannabinoid molecule, comprising:

providing a composition comprising cannabinoids and cellulose, in which the cannabinoids comprise a native cannabinoid molecule, the native cannabinoid molecule comprises a carboxyl group, and the native cannabinoid molecule is in a liquid phase or a solid phase;

suspending either a particle or a droplet of the composition comprising cannabinoids in a gas phase, in which the particle or droplet comprises the native cannabinoid molecule;

contacting the composition with sufficient energy to convert the native cannabinoid molecule into (i) a carbon dioxide molecule and (ii) a modified cannabinoid molecule in the gas phase while the particle or droplet is suspended in the gas phase;

separating the modified cannabinoid molecule in the gas phase from the cellulose, in which the separating occurs both (a) after converting the native cannabinoid molecule into (i) the carbon dioxide molecule and (ii) the modified cannabinoid molecule in the gas phase, and (b) prior to contacting the modified cannabinoid molecule with a heat sink;

collecting the cellulose;

contacting the modified cannabinoid molecule with the heat sink to condense the modified cannabinoid molecule into a condensed cannabinoid molecule in a liquid distillate; and collecting the liquid distillate.

13. The method of claim 12, in which contacting the composition with sufficient energy to convert the native cannabinoid molecule into (i) the carbon dioxide molecule and (ii) the modified cannabinoid molecule in the gas phase comprises contacting the composition with energy at a rate of less than 100 kilowatts of power per gram of the composition for a duration of less than 60 seconds.

14. The method of claim 12, in which contacting the composition with sufficient energy to convert the native cannabinoid molecule into (i) the carbon dioxide molecule and (ii) the modified cannabinoid molecule in the gas phase comprises contacting the composition with 0.0003 to 0.04 kilowatt hours of energy per gram of the composition.

15. The method of claim 12, comprising contacting the composition with a heated gas having a temperature of 190° C. to 250° C.

16. The method of claim 12, comprising contacting the composition with a heated surface having a temperature of 190° C. to 250° C.

17. The method of claim 12, in which the composition has a surface-area-to-volume ratio greater than 1000 per meter.

18. The method of claim 12, comprising both contacting the composition with the sufficient energy and condensing the modified cannabinoid molecule into the condensed cannabinoid molecule in less than 60 seconds.

19. The method of claim 12, comprising directing the composition comprising cannabinoids along a heated path having a length of at least 4 meters, in which the composition is contacted with the sufficient energy in the heated path.

20. The method of claim 19, comprising directing the composition comprising cannabinoids along the heated path at a rate of at least 2 meters per second.

21. The method of claim 12, in which the native cannabinoid molecule is cannabidiolic acid, the modified cannabinoid molecule is cannabidiol, and the condensed cannabinoid molecule is cannabidiol.

22. The method of claim 12, in which the native cannabinoid molecule is tetrahydrocannabinolic acid, the modified cannabinoid molecule is tetrahydrocannabinol, and the condensed cannabinoid molecule is tetrahydrocannabinol.

23. The method of claim 12, comprising converting at least 75% of the native cannabinoid molecule into the condensed cannabinoid molecule per mole.

24. The method of claim 12, comprising producing a liquid distillate comprising the condensed cannabinoid molecule and cannabinol at a molar ratio greater than 100:1.

25. The method of claim 12, comprising producing a product from the liquid distillate, in which the product comprises the condensed cannabinoid molecule at a concentration of at least 50% by weight.

26. The method of claim 25, in which the liquid distillate comprises ethanol, and the method comprises evaporating ethanol to produce a product.

* * * * *